United States Patent [19]

Jerabek

[11] Patent Number: 4,693,238
[45] Date of Patent: Sep. 15, 1987

[54] MAGNETOTHERAPEUTIC IMPULSE DEVICE

[75] Inventor: Jiri Jerabek, Prague, Czechoslovakia

[73] Assignee: TELSA, koncernovy podnik, Prague, Czechoslovakia

[21] Appl. No.: 772,246

[22] Filed: Sep. 3, 1985

Related U.S. Application Data

[63] Continuation-in-part of Ser. No. 515,940, Jul. 20, 1983, abandoned.

[30] Foreign Application Priority Data

Jul. 20, 1982 [CS] Czechoslovakia ............... 5549-82

[51] Int. Cl.$^4$ ............................................. A61B 17/52
[52] U.S. Cl. ........................................ 128/1.5; 128/1.3
[58] Field of Search ............... 128/1.3, 1.5, 422, 421, 128/420 R

[56] References Cited

U.S. PATENT DOCUMENTS

| 3,337,776 | 8/1967 | Elmi .............................. | 128/1.3 X |
| 3,468,301 | 9/1969 | Hollend ........................ | 128/1.5 |
| 4,095,588 | 6/1978 | Goldman et al. ............. | 128/1.5 |
| 4,316,453 | 2/1982 | Harrison ....................... | 128/1.3 |
| 4,323,056 | 4/1982 | Bornelli et al. ............... | 128/1.3 |
| 4,428,366 | 1/1984 | Findl et al. ................... | 128/1.5 |

FOREIGN PATENT DOCUMENTS

| 76400 | 4/1983 | European Pat. Off. ........... | 128/1.3 |
| 2707574 | 8/1978 | Fed. Rep. of Germany ..... | 128/1.3 |

Primary Examiner—Edward M. Coven

[57] ABSTRACT

Circuit arrangement of magnetotherapeutic impulse device for treatment of inflammatory and degenerative illnesses such as spondylitis, e.g. Bechterew's disease, operating on the principle of a pulsatory magnetic field, the frequency and intensity of which can be adjusted within an wide range, enabling the operator the adjustment and control of treatments for a number of different treated sites.

7 Claims, 4 Drawing Figures

4,693,238

MAGNETOTHERAPEUTIC IMPULSE DEVICE

CROSS-REFERENCE TO RELATED APPLICATION

This application is a continuation-in-part of application Ser. No. 515,940, filed July 20, 1983, abandoned.

BACKGROUND OF THE INVENTION

The invention relates to a circuit arrangement of a magnetotherapeutic impulse device, particularly adapted for treatment of inflammatory and degenerative illnesses, such as spondylitis, e.g. Bechterew's disease.

Known magnetotherapeutic devices of this kind are based either on the discharge of a capacitor to the winding of an electromagnet or on a connection of the winding of an electromagnet to a multivibrator circuit, which closes the current circuit of a thyristor coil by a multivibrator at a variable frequency or which closes the current of a coil by a thyristor controlled by an adjusted frequency of the AC line voltage or which closes direct current flowing to the winding of an electromagnet by a mechanical motor driven switch.

A drawback of existing devices involves controlling the power supplied to the electromagnet coils. there is no accurate way to adjust the repeating frequency of the magnetic field, and no way to automatically change the repeating frequency. With existing devices, another drawback is that a maximum of only four coils may be used. Some existing devices synchronize the current to coils with the phase of the supplied voltage and thus provide uniformity of impulses of the magnetic field. The majority of known devices uses mechanical switching, thus in creasing their size and reducing their reliability.

SUMMARY OF THE INVENTION

It is an object of this invention to eliminate or at least to reduce these drawbacks.

According to this invention a circuit for adjustment of the voltage, connected to a voltage source, is connected by its output to the clock input of an electronic selector switch and also to the clock input of a control block for the control of a multiplexor. The outputs of the electronic selector switch are connected both to inputs of phasing elements, and, starting with the second output, to inputs of the multiplexor. The outputs of the phasing elements are connected to the control inputs of power switching elements, which in turn are each connected in series with an electromagnet coil and are connected to the voltage source. The output of the multiplexor is connected to the zero input of the electronic selector switch.

A block indicating the adjusted frequency is connected to the output of the control block for control of the multiplexor.

A timing switch is connected between the output of the circuit for adjustments of the voltage and the clock inputs of the electronic selector switch and the control block for control of the multiplexor.

Circuits indicating the change-over are connected in parallel to phasing elements.

Separating elements are connected between the control inputs of the power switching elements and the outputs of the phasing elements.

A simple n-pole switch is connected by opposite contacts to the circuit of a recording unit in parallel to the electromagnet coils.

The advantages of this invention are primarily the ability to control the power for individual electromagnet coils and the ability to provide a continuous, automatic and manual control of the change of the repeating frequency of the generated magnetic field, securing an accurate dosing of the magnetic field at each location. Since a large number of electromagnet coils may be connected simultaneously, it is possible to apply the magnetic field to a large number of joints to be treated, for example to the whole spine. Because of the mentioned interconnection, it is possible to synchronize the power switching elements with the phase of the voltage supplied by the voltage source, providing uniformity of impulses to the electromagnet coils. By application of electronic elements for contactless switching and by digital control, a high reliability of operation and a minimum consumption of power are obtained.

BRIEF DESCRIPTION OF THE DRAWING

The circuit arrangement of the magnetotherapeutic impulse device according to this invention will be described in an exemplary embodiment in the attached drawings, where.

DESCRIPTION OF THE PREFERRED EMBODIMENT

Figure 1:
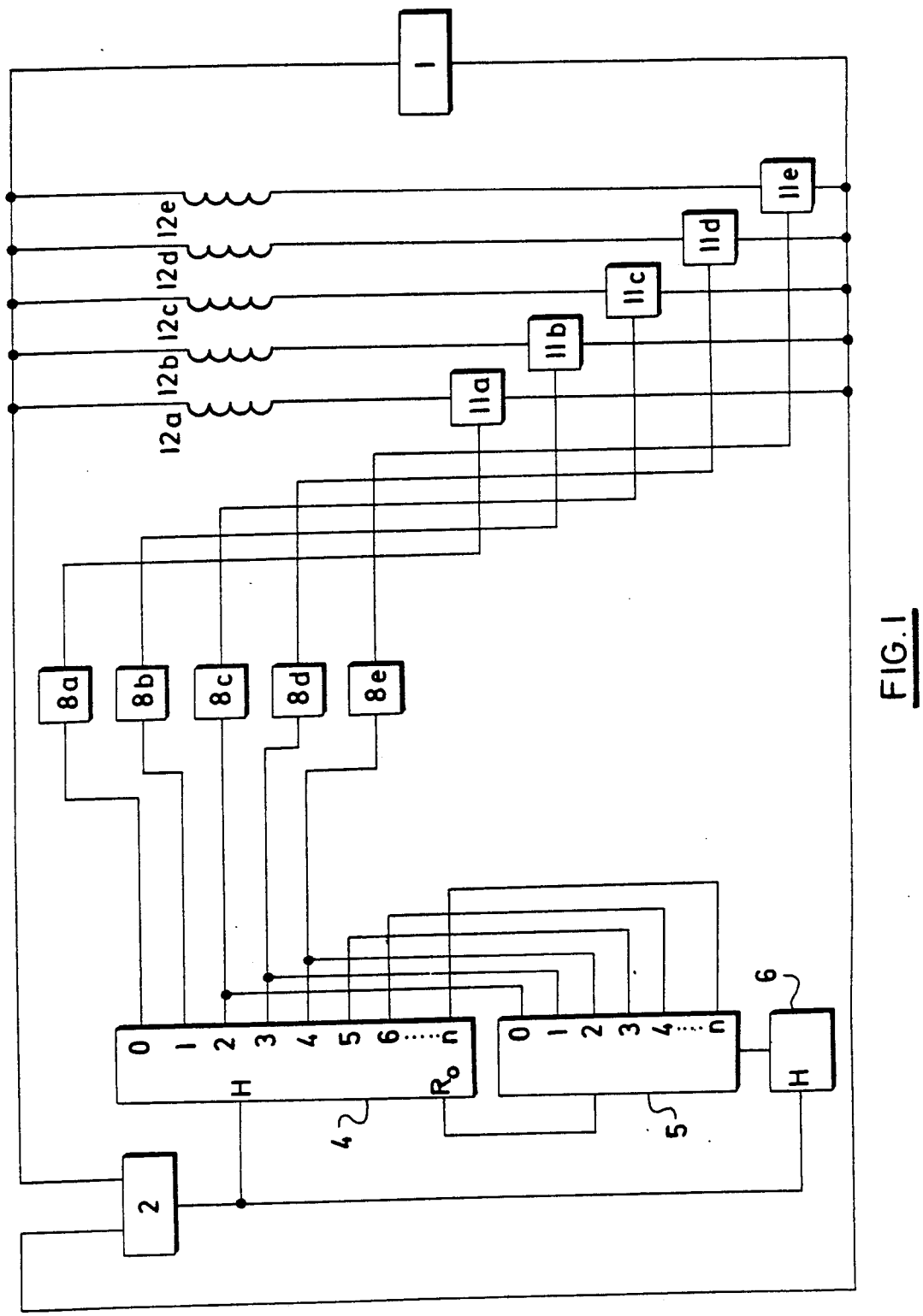
FIG. 1 shows a block wiring diagram of the fundamental interconnection of the magnetotherapeutic impulse device.

According to FIG. 1, showing the fundamental interconnection of the magnetotherapeutic impulse device, a circuit 2 for voltage adjustment, connected to a voltage source 1, is connected by its output both to the clock input of an electronic selector switch 4 and also to the clock input of a control block 6 which is connected to the control input of multiplexor 5. Outputs of the electronic selector switch 4 are connected both to inputs of phasing elements 8a to 8e, and, starting with the second output to the inputs of multiplexor 5. The outputs of the phasing elements 8a to 8e are connected to the control inputs of power switching elements 11a to 11e which are connected in series with electromagnet coils 12a to 12e and the voltage source 1. The output of multiplexor 5 is connected to the zero input of the electronic selector switch 4.

Figure 2:
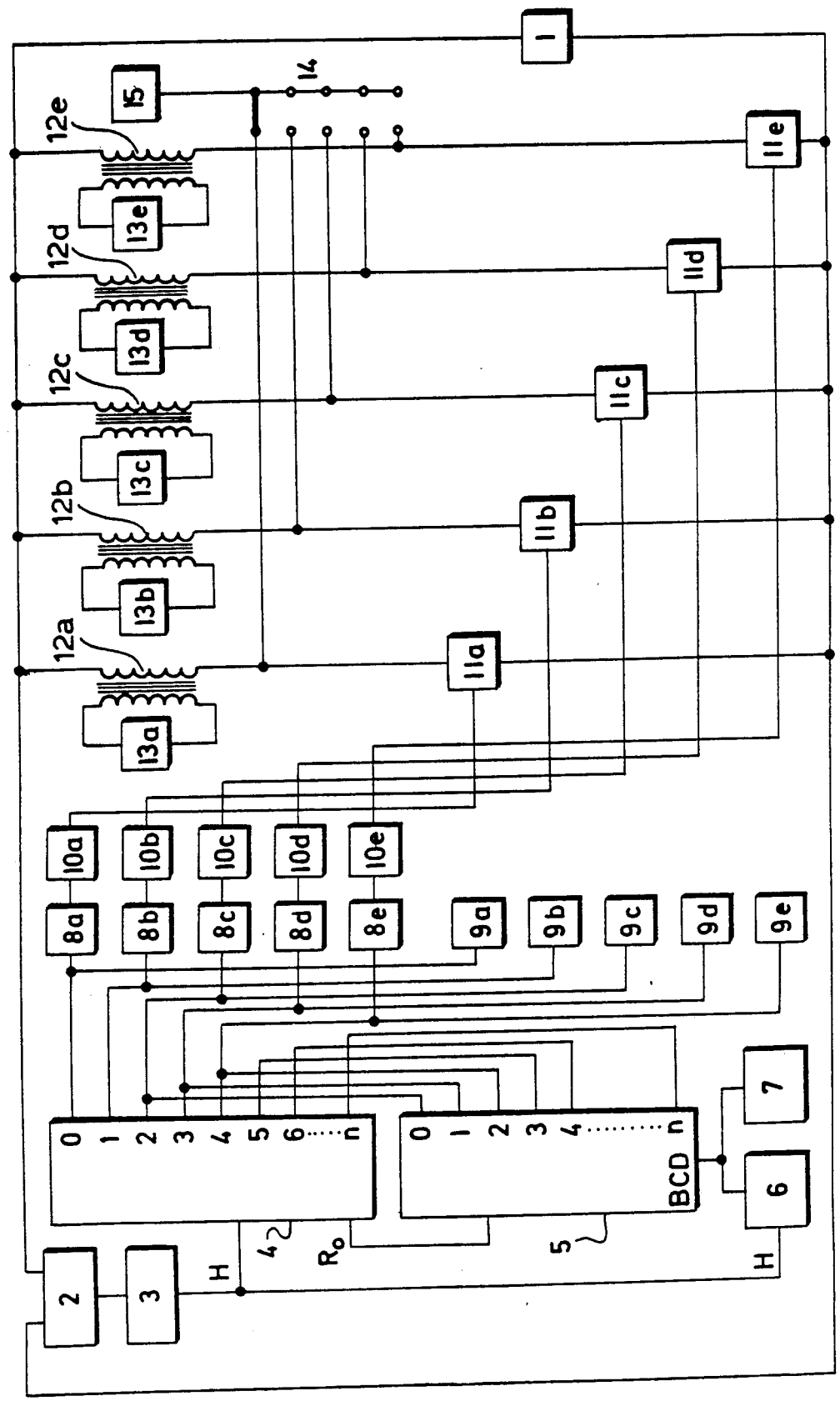
FIG. 2 shows an extended block wiring diagram as in FIG. 1 with application of additional circuits and elements.

In order to increase the effect, the fundamental circuit arrangement of the magnetotherapeutic impulse device is completed by the following circuit arrangements shown in FIG. 2:

A timing switch 3 is connected between the output of circuit 2 for voltage adjustment and the clock inputs of electronic switch 4 and control block 6.

A block 7 indicating the adjusted frequency is connected to the output of the control block 6 for control of the multiplexor 5.

Indicator circuits 9a to 9e, indicating the switching over are connected in parallel to the inputs of phasing elements 8a to 8e.

Separating elements 10a to 10e are connected between the control inputs of power switching elements 11a to 11e and outputs of phasing elements 8a to 8e.

Indicator circuits 13a to 13e are connected in parallel to the electromagnet coils 12a to 12e.

A simple five pole switch 14 is connected by opposite contacts to circuit 15, a recording unit, in parallel to the electromagnet coils 12a to 12e.

In operation of the circuit arrangement of the magnetotherapeutic impulse device, the circuit 2 for voltage adjustment connected to the voltage source 1, adjusts the supplied AC line voltage to the required magnitude and changes the shape from a sine wave to a rectangular wave. The adjusted voltage is then supplied both to the clock input of the electronic selector switch 4 and the clock input of the control block 6 for control of the multiplexor 5. At individual outputs of the electronic selector switch 4 a consecutive change-over of logic levels takes place, whereby the speed of the change-over depends on the frequency of the voltage supplied to the clock input of the electronic selector switch 4. The outputs O to n of the electronic selector switch 4 are connected to the inputs of phasing elements 8a to 8n. The phasing elements provide a time delay of the signals passing through them and thus also cause a phase shift of the switching elements 11a to 11n with respect to the phase of voltage supplied from the voltage source 1. Because of the series connection of coils 12a to 12n of the electromagnets with power switching elements 11a to 11n and the voltage source 1 it is possible to individually control power to the electromagnet coils 12a to 12n. Furthermore, starting with the second output, the outputs of the electronic selector switch 4 are connected to the inputs O to n of the multiplexor 5, the output of which is connected to the zero input of the electronic selector switch 4. The control of the multiplexor 5 is achieved by means of the control block 6 for the control of the multiplexor. The control block 6 for the control of the multiplexor is connected by its clock input to the circuit 2 for the adjustment of the voltage and by its output to the control input of the multiplexor 5 and, by means of the multiplexor 5, provides transmission of logic levels from the outputs of the electronic selector switch 4 to the zero input of the electronic selector switch 4 and thus, according to adjustment of the control block 6 for control of the multiplexor, alows for the operator to increase or decrease the rate of the change-over cycle of the electronic selector switch 4. By this kind of interconnection it is possible to synchronize the excitation of the magnetic fields by the electromagnet coils 12a to 12n and to adjust the power to individual electromagnet coils 12a to 12n by means of phasing elements 8a to 8e. By connection of the electronic selector switch 4 with the multiplexor 5 and by its control by the control block 6 for control of the multiplexor it is possible to shorten or lengthen the change-over cycle of the electronic selector switch 4 and thus to change the repeating frequency of the excited magnetic fields by electromagnet coils 12a to 12n.

The additional circuits shown in FIG. 2 provide the following amplification of function:

Information about the adjusted frequency is secured by connection of the block 7, for indication of the adjusted frequency, to the output of the control block 6 for control of the multiplexor 5.

The adjustment of the time the patient is exposed to treatment is secured by the introduction of the timing switch 3 between the outputs of circuit 2, for adjustment of the voltage, and the clock inputs of the electronic selector switch 4 and control block 6.

Information about the operation of the logic part of the device is secured by the parallel connection of the circuit 9a to 9n for indication of change-over to inputs of phasing elements 8a to 8n.

The separation of logic parts of the device from power parts of the device is achieved by introduction of separating elements 10a to 10n between the control inputs of power switching elements 11a to 11n and the outputs of phasing elements 8a to 8n.

Information about the excited magnetic fields and about possible failure of the power switching elements 11a to 11n is secured by a parallel connection of indicator elements 13a to 13n to the electromagnet coils 12a to 12n.

Information about the shape and amplitude of the voltage on individual electromagnet coils 12a to 12n is secured by parallel connection of a simple n-pole switch 14 to electromagnet coils 12a to 12n and by connection of its opposite, mutually interconnected contacts to circuit 15, a recording unit.

Figure 3A:
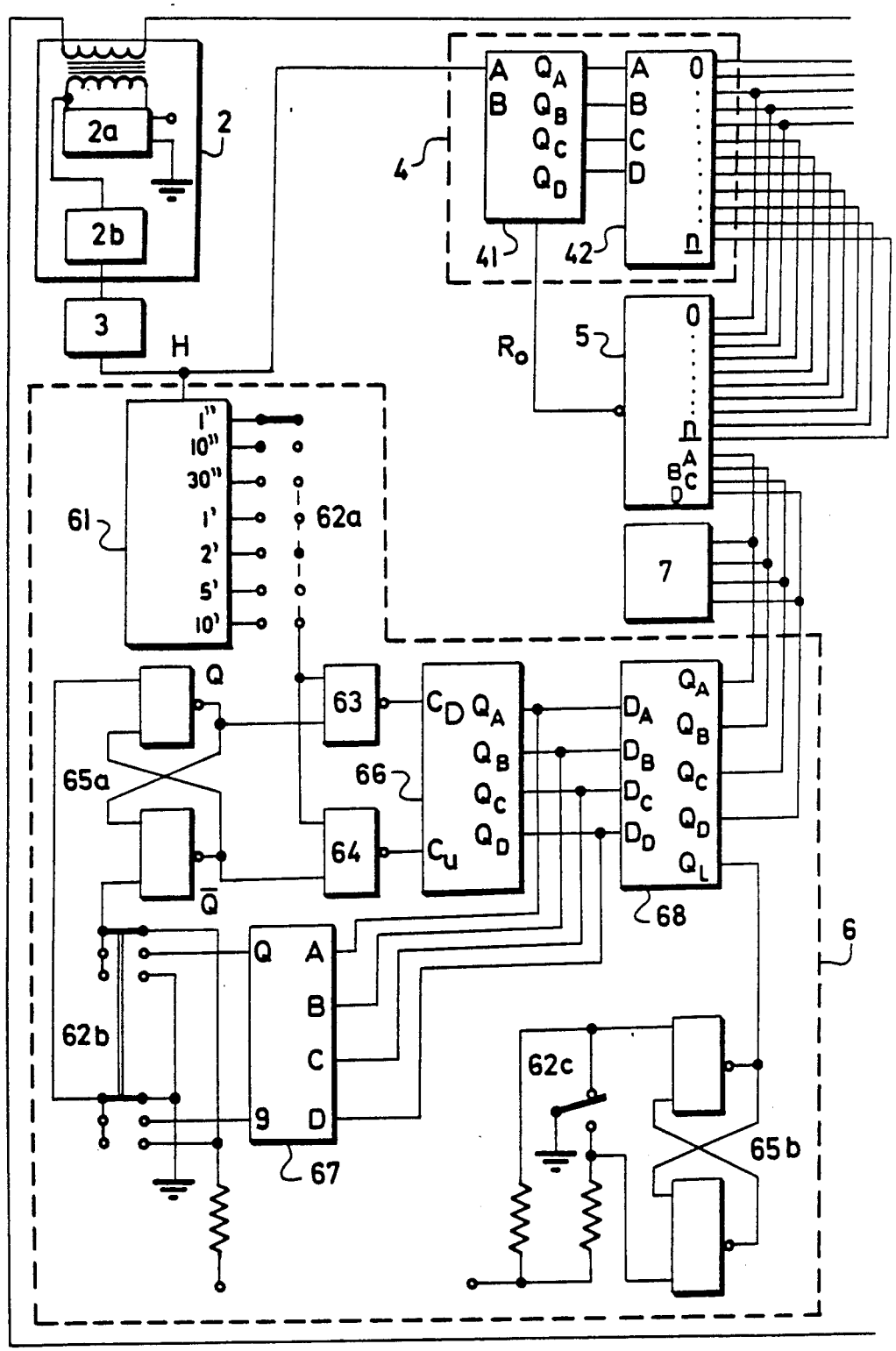
FIGS. 3a and 3b taken together show a concrete exemplary interconnection of the magnetotherapeutic impulse device.
Figure 3B:
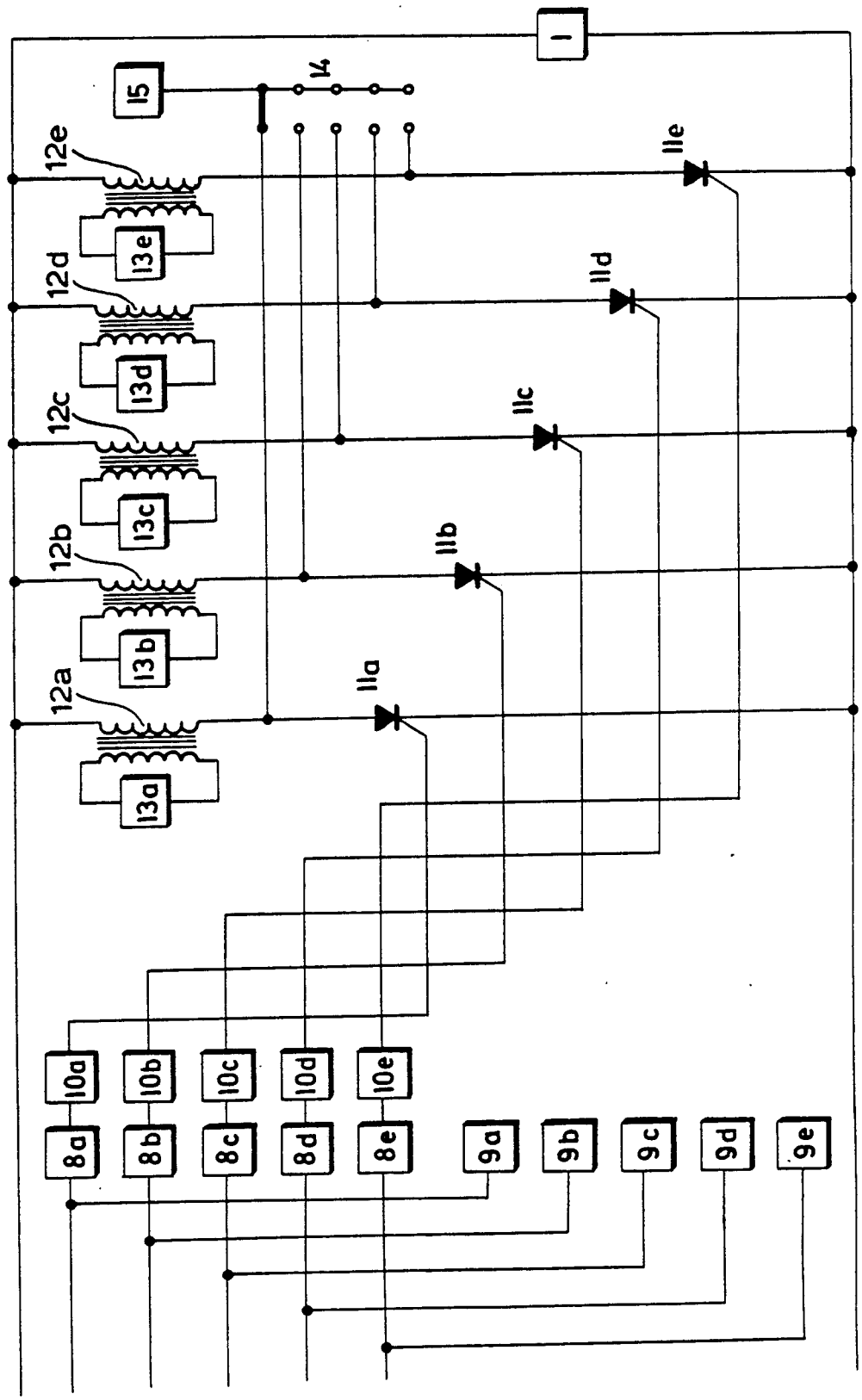

An example of a practical interconnection of a magnetotherapeutic impulse device according to this invention is shown in combined FIGS. 3a and 3b.

The AC line voltage from the voltage source 1 is supplied to the input of circuit 2 for adjustment of voltage comprising a main transformer. From the secondary winding of the main transformer a stabilized rectifier 2a is connected for feeding low current DC parts of the device. A voltage sample for the pulse shaper 2b for changing the sine voltage to a rectangular shape is also taken from the secondary winding of the main transformer. The thus adjusted voltage is supplied to the input of the timing switch 3, by way of which it passes for a predetermined time to the output and therefrom both to the clock input of the selector switch 4 and to the clock input of block 6 for control of the multiplexor 5.

The electronic selector switch 4 comprises a counter 41 and a code converter 42 (one of n), wherein the BCD inputs of the code converter 42 are connected to the BCD outputs of the counter 41. The supplied clock frequency is coded by the counter 41 to a BCD code and the code converter 42 (one of n) switches over the logic levels of its outputs in rhythm with the supplied clock frequency. The outputs of the electronic selector switch 4 are connected to the inputs of phasing elements 8a to 8n, to which inputs of circuits 9a to 9n for indication of the change-over are connected in parallel.

The phasing elements 8a to 8n secure the phase displacement of the signal on their outputs with respect to the phase of the signal on their inputs and thus also with respect to the phase of the AC line voltage supplied from the voltage source 1. The outputs of the phasing elements 8a to 8n are connected to the inputs of separating elements 10a to 10n, the outputs of which are connected to the control inputs of power switching elements 11a to 11n.

The separating elements 10a to 10n secure the transmission of the signal from the phasing elements 8a to 8n to the control inputs of power switching elements 11a to 11n and separate the control electronics from the power part of the circuit. By supplying a signal to the control inputs of power switching elements 11a to 11n, these elements are brought to conductive condition and due to their series connection with the electromagnet coils 12a to 12n and with the voltage source 1, electric current passes through the circuit which excites the magnetic field.

The indicator circuits 13a to 13n connected in parallel to coils 12a to 12n indicate excitation of the magnetic field and simultaneously serve as indicators in case of a possible failure of power switching elements 11a to 11n.

According to the position of a simple n-pole switch 14 connected to electromagnet coils 12a to 12n by its opposite contacts to the circuit 15 recording unit, the operator may obtain information about the amplitude and shape of the voltage impulse at individual electromagnet coils 12a to 12n.

In control block 6 for control of the multiplexor 5, the clock frequency supplied from the output of the timing switch 3 is supplied to the input of the separating section 61 and therefrom voltage of rectangular shape and of a frequency 1", 10", 30", 1', 2', 5', or 10' is selected from individual outputs and supplied to contacts of a simple multipole switch 62a, the opposite contacts of which are mutually interconnected. By means of the switch 62a, the voltage of a chosen frequency is supplied to the first inputs of positive two input gates 63 and 64, the second inputs of which the control circuit 65a is connected by its outputs Q and Q. The outputs of positive two input gates 63 and 64 are connected to inputs $C_D$ and $C_U$ of a reversible counter 66. The switching over of the control circuit 65a is accomplished by means of the switch 62b which secures in both extreme positions that an outputs Q and Q of the control circuit 65a will be either the logic level L and H or H and L, and thus transmission of the signal will be either by the positive two input gate 63 or 64 to the input $C_D$ or $C_U$ of the reversible counter 66, whereby a counting up or down is secured. In the middle position of the selector switch 62b, the automatic change-over of conditions of outputs Q and Q of the control circuit 65a is by means of connected outputs 0 and 9 of the converter 67 (one of n) to the middle contacts of the selector switch 62b. The BCD input of the converter 67 (one of n) is connected to the BCD output of the reversible counter 66, whereby, for instance, in case of counting ahead after reaching a binary code number n=9 the automatic change-over of the reversible counter 66 for the operation of counting down is secured, furthermore, after reaching the binary number n=0 the automatic change-over for counting up is secured and the whole cycle is constantly repeated.

The BCD outputs of the reversible counter 66 are also connected to the inputs of the memory 68. By means of the selector switch 62c and the circuit 65b for locking the memory 68 it is possible to prevent transmission of a binary coded number form the input of the memory 68 to the output of the memory 68 and to maintain the thus chosen number on the output of the memory 68 without regard to the actual condition of the BCD outputs of the reversible counter 66. The outputs of the memory 68 are connected both to the inputs of blockk 7 for indicating the adjusted frequency and to the BCD inputs, of multiplexor 5.

Outputs of the electronic selector switch 4, starting with the second output are connected to the outputs O to n of the multiplexor 5. The output of the multiplexor 5 is connected to the zero input of the electronic selector switch 4. The functioning of the thus interconnectted multiplexor 5 is that the supplied logic levels from the outputs of the electronic selector switch 4 are transmitted to the output of the multiplexor solely from the output which corresponds to the binary code number on the BCD input of the multiplexor 5. The logic level H supplied from its output to the zero input of the electronic selector switch 4 or 41 respectively is thus eliminated, meaning a return of the change-over of the electronic selector switch or to the output zero.

Depending on which the input of the multiplexor 5 transmits, there is a speeding or slowing of the counting cycle of the counter 41 and thus also by way of the converter 42 (one of n), there is in the phasing elements 8a to 8n, separating elements 10a to 10n, and control inputs from the power switching elements 11a to 11n an increase or reduction of the repeating frequency of the excited magnetic field by the electromagnet coils 12a to 12n.

The interconnection of the magnetotherapeutic device provides for the selection of the repeating frequency of the magnetic field as a fraction of the frequency of the voltage of the voltage source 1. It is possible to select a single frequency by locking the memory 68 by the switch 62c via the circuit 65b for locking the memory. Alternatively, it is possible to select, based on the adjustment of the switches 62a and 62b, at intervals determined by the dividing sections 61, an automatic increase or decrease of the repeating frequency of the excited magnetic field or automatic increase following decrease or vice versa. By means of adjustment of the phasing elements 8a to 8n it is possible to secure the phase displacement of the power switching elements 11a to 11n with respect to the phase of the supply voltage from voltage source 1 and thus adjust the power supplied to the individual electromagnet coils 12a to 12n. By adjustment of the timing switch 3 a standstill of the arrangement after a prior determined time is secured. The circuit 7 for indication of the adjusted frequency indicates the repeating frequency of the excited magnetic field. The circuits 9a to 9n for indicating the change-over indicates a correct functioning of the electronic selector switch 4. The indicating circuits 13a to 13n indicate the presence of the excited magnetic field.

By means of a simple n-pole selector switch 14 and by the circuits 15 recording unit it is possible to check the amplitude and shape of the voltage impulses on electromagnet coils 12a to 12e.

As above indicated, the apparatus of the invention is particularly adapted for treatment of inflammatory and degenerative diseases, such as spondylitis, e.g. Bechterew's disease. The following definitions are found in Stedman's Medical Dictionary (The Williams and Wilkins Co., 23rd Edition, 1976, page 1319).

Spondylitis s. Inflammation of one or more of the vertebrae; deformans, poker back; Bechterew's disease; Struempell's disease (1); arthritis and osteitis deformans involving the spinal column; it is marked by nondular deposits at the edges of the intervertebral disks, with ossification of the ligaments and bony ankylosis of the intervertebral articulations, and results in a rounded kyphosis with rigidity.

The following tables I to 5, inclusive, show the results of the treatments of patients suffering from Bechterew's disease by the use of the apparatus of the invention.

The following abbreviations are used in the tables:
SD—standard deviation
t—critical value calculated from results for Student t-test
ut—calculated critical values for Wilcoxon non-parametric test
Laterofl.dx.—flexion of body to the right Laterofl.sin.—flexion of the body to the left Head rot.dx. (deg)—rotation of the head in angle degrees to the right head rot.sin. (deg)—rotation of the head in angle degrees to the left

TABLE 1

Statistical evaluation of spine movability and scale of pain in control group. Used t-test and Wilcoxon's test. ($x_a$-mean before; $x_p$-mean after "treatment")

| Distance | $x_a$ | SD | $x_p$ | SD | $x_p - x_a$ | SD | t | $u_t$ |
|---|---|---|---|---|---|---|---|---|
| Schober | 0.928 | 0.821 | 0.928 | 0.863 | 0.000 | 0.267 | 3.851E-7 | 14 |
| Stibor | 2.321 | 0.671 | 2.393 | 0.603 | 0.071 | 0.319 | 0.806 | 7 |
| Thomayer | 21.000 | 9.449 | 22.286 | 10.229 | 1.286 | 3.825 | 1.212 | 30 |
| Laterofl. dx. | 10.143 | 4.878 | 9.214 | 4.109 | −0.929 | 2.344 | 1.428 | 17 |
| Laterofl. sin. | 11.857 | 6.334 | 11.500 | 6.310 | −0.357 | 3.734 | 0.345 | 50.5 |
| Head rot. dx. (deg) | 21.429 | 17.158 | 20.357 | 12.459 | −1.071 | 8.697 | 0.444 | 27 |
| Head rot. sin. (deg) | 35.307 | 17.775 | 35.000 | 17.113 | −0.357 | 8.755 | 0.147 | 32.5 |
| Chin-sternum | 4.571 | 2.945 | 4.000 | 2.828 | −0.571 | 1.348 | 1.529 | 16.5 |
| Fleche | 7.429 | 6.366 | 7.786 | 5.453 | 0.357 | 2.942 | 0.438 | 46 |
| Scale of pain | 52.000 | 28.086 | 43.733 | 26.851 | −8.267 | 14.789 | 2.091 | 33 |

TABLE 2

Statistical evaluation of total effect of magnetotherapy of m. Bechterew. Used $Chi^2$ test.

| | Positive | No + negative |
|---|---|---|
| Control Group | 4 | 10 |
| Treated Group | 82 | 5 |

Chi-2 41.140 (significant on 1% level)
Positive effect-decrease or loss of pain, increase of movability of spine, decrease of drug consumption.

TABLE 3

Statistical evaluation of total effect of magnetotherapy of m. Bechterew. Expressed in %, used modified t-test.

| | Positive | no + negative |
|---|---|---|
| Control Group | 28.571 | 71.429 |
| Treated Group | 94.253 | 5.747 |

Test criterium = 65,682 (significant on 1% level)
Crit. value - 27,239

TABLE 4

Statistical evaluation of negative effects of magnetotherapy of m. Bechterew. Used $Chi^2$ test.

| | Positive + no | Negative |
|---|---|---|
| Control Group | 14 | 0 |
| Treated Group | 86 | 1 | chi-2 0.163 (No significance)
Negative effect - 1 patient with arisen paravertebral myositis during magnetotherapy.

TABLE 5

Statistical evaluation of negative effects of magnetotherapy of m. Bechterew. Expressed in %, used modified t-test.

| | Positive + no | Negative |
|---|---|---|
| Control Group | 100.000 | 0.000 |
| Treated Group | 98.851 | 1.149 |

Test criterium = 1.149 (no significance)
Crit. value = 5.821 (5%)

Although the invention is described and illustrated with reference to a plurality of embodiments thereof, it is to be expressly understood that it is in no way limited to the disclosure of such preferred embodiments but is capable of numerous modifications within the scope of the appended claims.

We claim:

1. Circuit arrangement of a magnetotherapeutic impulse device for treatment of spondylitis, e.g. Bechterew's disease, comprising a voltage source; and circuit means for voltage adjustment;

an electronic selector switch having a plurality of outputs, a zero input and a clock input; a multiplexor; and multiplexor control means, said multiplexor control means also having a clock input;

the circuit means for voltage adjustment being connected by its input to the voltage source and by its output both to the clock input of the electronic selector switch and to the clock input of the multiplexor control means;

a plurality of phasing elements, each output of the electronic selector switch being connected to a corresponding input of one of said phasing elements;

a plurality of power switching elements, each having a control input, the output of each of said phasing elements being connected to a corresponding control input of one of said power switching elements;

a plurality of electromagnet coils each one of which is connected in series with a corresponding one of said power switching elements and the voltage source;

the outputs of the electronic selector switch being furthermore connected, starting with the second output, to the inputs of the multiplexor, the output of the multiplexor being connected to the zero input of the electronic selector switch.

2. Circuit arrangement of a magnetotherapeutic impulse device as in claim 1, including indicator means being connected to the output of the multiplexor control means.

3. Circuit arrangement of a magnetotherapeutic impulse device as in claim 1, including a timing switch connected between the output of the circuit means for voltage adjustment and the clock inputs of the electronic switch and the multiplexor control means.

4. Circuit arrangement of a magnetotherapeutic impulse device as in claim 1, including indicator means connected in parallel to the inputs of the phasing elements.

5. Circuit arrangement of a magnetotherapeutic impulse device as in claim 1, including separating means connected between the control inputs of the power switching elements and the outputs of phasing elements.

6. Circuit arrangement of a magnetotherapeutic impulse device as in claim 1, including indicator means connected to the electromagnet coils for indicating when said coils are activated.

7. Circuit arrangement of a magnetotherapeutic impulse device as in claim 1, including an n-pole selector switch and recording means, the selector switch being connected to the recording means and, at each pole parallel to the individual electromagnet coils.

* * * * *